US006827697B1

(12) United States Patent
Liepman

(10) Patent No.: US 6,827,697 B1
(45) Date of Patent: Dec. 7, 2004

(54) CONTROLLED THERAPEUTIC TRACTION DEVICE

(76) Inventor: Dennis Lynn Liepman, 4917 Vista Arroya Rd., La Mesa, CA (US) 91941

( * ) Notice: Subject to any disclaimer, the term of this patent is extended or adjusted under 35 U.S.C. 154(b) by 178 days.

(21) Appl. No.: 10/138,586

(22) Filed: May 3, 2002

Related U.S. Application Data

(60) Provisional application No. 60/288,972, filed on May 4, 2001.

(51) Int. Cl.[7] .................................................. A61F 5/00

(52) U.S. Cl. .......................... 602/32; 606/241; 482/92; 482/93; 482/111

(58) Field of Search ............................. 602/32, 35, 36; 601/5, 84; 606/237, 241; 482/92, 93, 111

(56) References Cited

U.S. PATENT DOCUMENTS 1,347,913 A * 7/1920 Rink .......................... 602/36
3,403,675 A * 10/1968 Carr ............................ 602/32
3,859,990 A * 1/1975 Simon ........................ 601/157
5,078,126 A * 1/1992 Perry ......................... 606/241
5,258,018 A * 11/1993 Van Nostrand ............. 606/241
5,658,245 A * 8/1997 McGinnis et al. ............ 602/32
6,042,602 A * 3/2000 Wells ......................... 606/241
6,151,726 A * 11/2000 Ajima ........................... 4/488

* cited by examiner

*Primary Examiner*—Henry Bennett
*Assistant Examiner*—Kathryn Odland
(74) *Attorney, Agent, or Firm*—Mark H. Miller; Jackson Walker LLP

(57) ABSTRACT

The present invention is for a controlled therapeutic traction device utilizing a warmed hypertonic solution or other fluid of sufficient specific gravity to float the patient in a relaxing, relatively weightless environment. Traction is applied to a portion of the patient's body using various means to apply tension to that portion of the body, while the remainder of the patient's body continues to be suspended in the fluid.

18 Claims, 4 Drawing Sheets

CONTROLLED THERAPEUTIC TRACTION DEVICE

This application claims benefit of Ser. No. 60/288,972, filed May 4, 2001.

BACKGROUND OF THE INVENTION

1. Field of the Invention

Applicants' invention relates to a device for a therapeutic spa. More particularly, it relates to an apparatus for suspending a patient in a reduced weight environment while applying traction to a specific portion of the patient's body.

2. Background Information

Traction is applied as a force along an axis of the body. It can be applied selectively to the body by choosing points along the body at which the traction force is applied. The traction force may be applied as a constant tension through such means as weights or pulling on the body from an anchored object or, the tension may be elastic in nature such as with rubber tubing or other elastic appliances.

Traction has long been used by the medical community. It uses an applied tension at a specific point on the body in order to move a body part from an undesirable position to a desired position and hold it at the desired position. As a treatment, traction is variably and selectively applied through the placement of the tension, the amount of tension applied to the body part and the length of time the tension is applied. For example, traction may be used to relocate a broken bone or dislocated joint. Conventional traction systems use combinations of weights and pulleys to realign the bones and to immobilize them. Thus, fractured and dislocated bones are allowed to heal in the correct position and alignment.

Traction can also be used in the treatment of muscles. When the force of the traction is applied to a muscle group, the muscle group is stretched and maintained in the stretched position. Such treatment can help alleviate muscle strains and spasm.

Unfortunately, the nature of traction can make its application uncomfortable for the patient. Generally, while it is desirable to apply traction to a specific point along the body, or along a specific axis, the desired axis does not extend the entire length of the body, but the traction force is applied not only to the desired portion, but beyond as well. Additionally, the traction force that is applied over time can become uncomfortable for the patient. The patient is subject to the force determined by the medical provider and is dependant upon the medical provider to modify the amount of force applied.

Another modality of treatment that is often used for muscles is temperature. Heat applied to a muscle group tends to relax the muscle group allowing it to stretch more easily. Its effects can be used to enhance the traction's effect on the body. Additionally, the warmth can help the patient relax.

Thus, there is a need for a device that allows for the application of traction to a specific portion of the body, but that allows the remainder of the body to rest relatively free from the traction force. And, while the determination of the amount of force to be applied in traction should be determined by the medical provider, it would be advantageous for a device that allows the patient to modify the amount of force within a range set by the medical provider as tolerable to the patient.

SUMMARY OF THE INVENTION

The present invention is an apparatus that allows the medical provider to place a selected portion of a patient's body in traction while allowing the remainder of the patient's body to rest, suspended in relative comfort. The present invention is a therapeutic spa that utilizes fluid to reduce the relative weight of the patient. By modifying the fluid, or the specific gravity of the fluid, the relative weight of the patient can be modified. The patient can thus float in a relaxing, relatively weightless environment. Traction can be then be applied to the patient, particularly the spine and lower extremities. Further, the fluid can be warmed to a desired temperature further providing a relaxing environment for the patient, as well as relaxing the patient's muscle groups in order to allow the muscle to stretch more easily and make the traction more effective.

The apparatus of the present invention incorporates a substantially vertical tub spa filled with a warm fluid. It is anticipated that different types of fluids maybe used. Water is one such fluid. It intended that the fluid be chosen, in part, for its specific gravity. If an aqueous solution is used for the fluid, the tonicity of the solution may be established in order to obtain the desired specific gravity. Changing the specific gravity of the fluid will effectively alter the buoyancy of the patient. Thus, patients of different body types and masses can be made to float at a desired level. For example, the specific gravity of the fluid can be altered in order that the patient float with neck and head above the fluid.

The heating of the fluid can help the patient be induced into a state of relaxation. Sufficient warming of the muscles, ligaments, and tendons will encourage this relaxed state, and promote their susceptibility to therapeutic traction.

As an example of the force of the present invention is applied to the lower extremities. While this may cause the patient to seek lower in the fluid, the amount of force and the specific gravity of the fluid can both be altered in order that the patient still floats sufficiently high enough in the fluid so as to be comfortable and safe. The traction, if applied to the lower extremities, pulls the legs downward, while the remainder of body floats otherwise relatively weightless in the fluid. Thus, traction is gently applied to the major joints of the lower extremities. The traction can be applied to other portions of the body as well and those portions of the body to which traction is not applied will continue to float and remain relatively weightless in the hypertonic solution.

The present invention provides a novel apparatus that will allow for the application of traction to a desired portion of the body while floating the remainder of the body, relatively weightless, in a hypertonic solution. The present invention further provides for:

a. warming of the fluid;

b. the ability to apply various types of traction;

c. the ability to apply traction to various part of the body;

d. heating the fluid for relaxation and more effective relief to joint and muscle pain;

e. circulation of the fluid;

f. filtering of the fluid;

g. sterilization of the fluid;

h. maintenance of the fluid level; and i. application of an electric charge or field to the patient.

DETAILED DESCRIPTION OF THE PREFERRED EMBODIMENT

Figure 1:
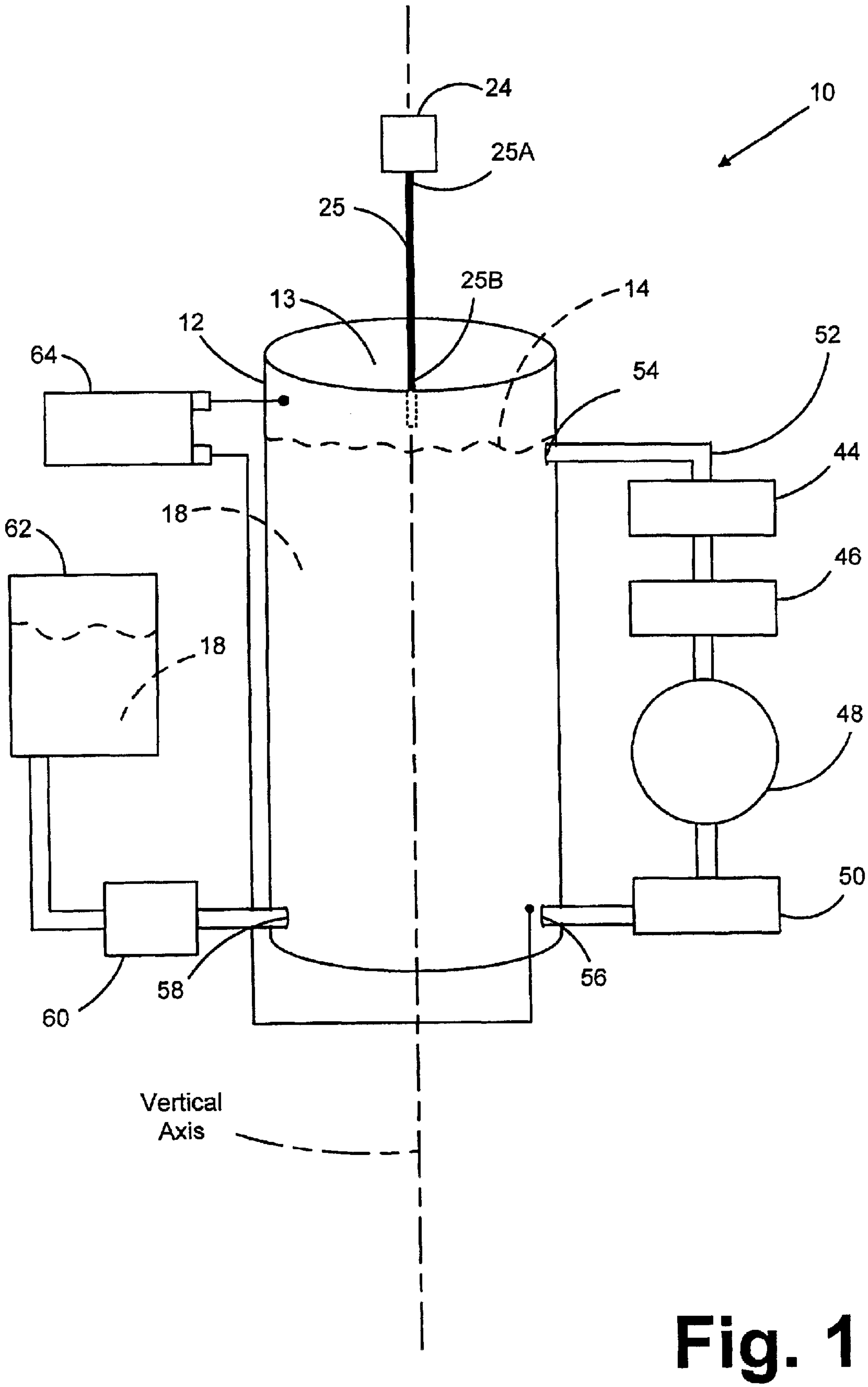
FIG. 1. is a schematic view of the present invention.

Referring to the figures, FIG. 1. illustrates the controlled therapeutic traction device (10). The tub (12) is designed to hold the fluid (18). An aperture (13) is provided so that a patient (16) can enter the tub (12). Thus, the aperture (13) must be sized in order to allow the patient (16) to enter and exist through the aperture (13). Furthermore, the tub (12) is sized to allow the patient (16), or a portion of the patient (16) to fit inside the tub (12). Generally, the controlled therapeutic traction device (10) will be used with the patient (16) in an upright position. Therefore, it is anticipated that the tub (12) will be elongated along a vertical axis and the tub (12) will be generally upright to match the patient's (16) position. However, operation of the controlled therapeutic traction device (10) is not dependent upon a specific shape or size of the tub (12). While not intended to be limiting, in one embodiment the tub (12) would be in the range of 42 inches to 92 inches tall and 30-inches to 42-inches in diameter. In the same embodiment the thickness of the tub (12) wall would be 0.375 inches to 0.057 inches thick. Because the fluid (18) is heated it may be desirable that the tub (12) be insulated in order to better maintain the fluid (18) temperature, and to reduce the power requirements needed for heating the fluid (18).

A traction member (24) is positioned substantially along the vertical axis above the aperture (13) of the tub (12). A traction line (25) is attached by its first end (25A) to the traction member (24). The traction line (25) extends from the traction member (24) through the aperture (13) of the tub (12). The second end (25B) of the traction line (25) may be positioned in the interior of the tub (12) or externally to the tub (12) above the aperture (13).

Fluid (18) is contained within the tub (12). The fluid (18) can be circulated through an optional series of optional devices by a pump (48). A circulation outlet (54) is provided that allows the fluid (18) to flow into a pipe (52). Fluid (18) flows through the pipe (52) as a result of the operative engagement of the pump (48) and is returned to the tub (12) through a circulation inlet (56). As the fluid (18) flows through the pipe (52) it can be filtered by an optional filter (44), sterilized by an optional sterilizer (46) and heated by an optional heater (50). In order to maintain the relative sterility of the fluid (18), it is anticipated that a number of sterilizing modalities could be employed. Examples are application of arc sterilizer, chlorine, ultraviolet light, silver ionization of the fluid, and the like. Likewise, the filter (44) may employ various modalities for removing undesirable particulate matter from the fluid (18). The heater (50) is used to warm the fluid (18). While utilization of the circulation of the fluid (18) is not necessary for the use of the controlled therapeutic traction device (10), use of the pump (48), filter (44), sterilizer (46), and heater (50) in various combinations is desirable. It is also desirable to maintain a desirable fluid level (14) in the tub (12). Because there is likely to be fluid (18) lost, and patients (16) can have varying body sizes and masses, a reservoir (62) maybe in operative engagement with the tub (12). The reservoir (62) contains additional fluid (18) and fluid (18) from the reservoir (62) can be pumped into the tub (12) by a reservoir pump (60) through a reservoir inlet (58) in order to raise the fluid level (14) of the tub (12). Conversely, the fluid level (14) in the tub (12) could be lowered by reversing the reservoir pump (62) and withdrawing fluid (18) from the tub (12) through the reservoir inlet (58) and into the reservoir (62).

A charge generator (64) may also be in operative engagement with the controlled therapeutic traction device (10). The charge generator (64) can be used to apply a relatively small electrical charge to the fluid (18) in order for therapeutic application of an electric field to the patient (16).

The type of fluid (18) used in the tub (12) may be varied. One option is an aqueous solution. A hypertonic solution with a specific gravity sufficient for floating a patient (16) may be created by using sodium chloride or magnesium sulfate as a solute. It is expected that an optimum specific gravity may be determined on a patient (16) by patient (16) basis. Or, it may be determined that the fluid (18) can have a range of specific gravities that are adequate to sufficiently float a wide range of patient (16) body sizes and masses. For example, a specific gravity could be determined for those patients (16) 25% under their ideal body weight, those at ideal weight, and those 25% over their ideal body weight. Once an optimum specific gravity of the fluid (18) is determined, various types of fluid, have the same specific gravity, can be chose and optimized for a specific patient (16) or group of patients (16). Regardless of the type of fluid (18) used, the specific gravity of the fluid (18) should be sufficiently high enough in order to float the patient (16) at a desired level. Fluids (8) with specific gravities of 1.2 or greater may be used in the controlled therapeutic traction device (10). Other additives to the fluid (18) may also be employed. For example, emollients, moisturizers, meditations, and cleansers, as well as other topical substances could be incorporated into the fluid (18) for application to the patient (16). Thus, skin irritations can be reduced or treated, as well as achieving other beneficial results.

Figure 2:
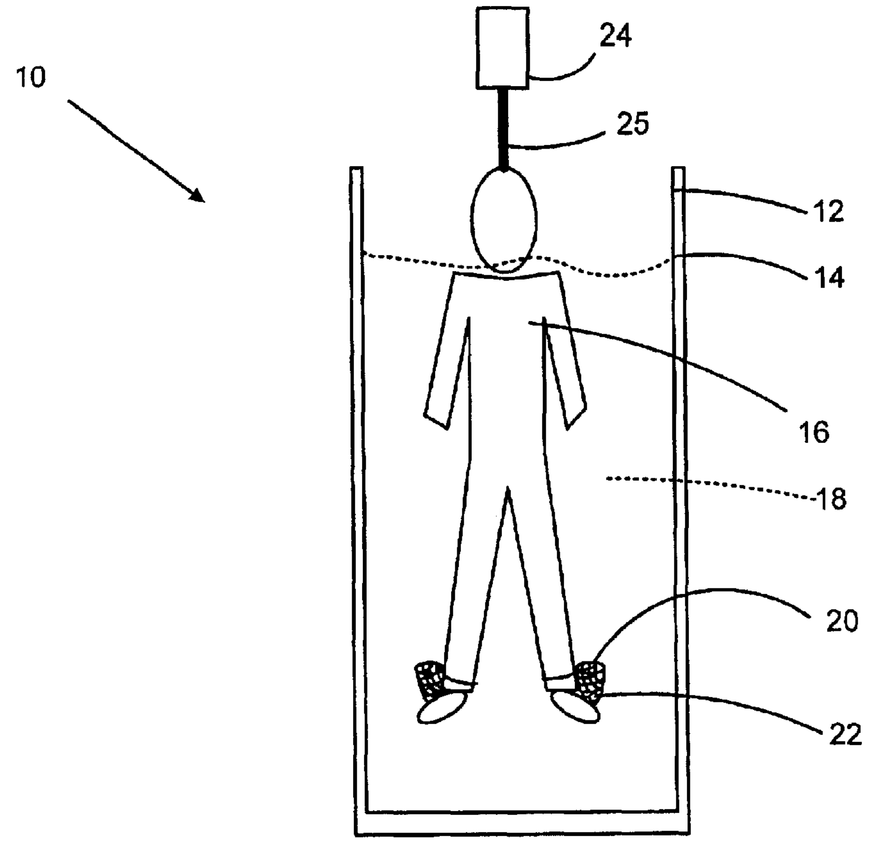
FIG. 2. is a cross sectional view tub portion of the present invention.

FIG. 2. illustrates a patient (16) suspended in the controlled therapeutic traction device (10). In this embodiment, the patient (16) is floating in the fluid (18) with the patient's (16) head and neck above the fluid level (14). The sides of the tub (12), in cross section, are also illustrated. A traction applicator (20) is attached to the patient's (16) legs. In this figure, traction is illustrated as being applied by weight (22), however, it is anticipated that many differing sources of tension could be applied to the patient (16). For example, an elastic band (not shown) or tether (not shown) could be attached to the tub (12) and to the patient (16) and tightened in order to apply tension to the patient (16). The weight (22) is applied by attaching the weight (22) to the patient by a variety of means such as leg baskets (shown in this figure as the traction applicator (20)), weighted garments (not shown), straps (not shown), or a multitude of other embodiments of the traction applicator (20) for attaching weight (22) to the patient (16).

Traction to the patient's (16) upper torso and spine is applied by the patient's (16) suspension from the traction member (24). The traction line is attached by a first end (25A) to the traction member (24) and by a second end (25B) to the patient (16). The traction member (24) is at a fix point outside the tub (12) and allows for the attachment of various traction devices (not shown).

Figure 3:
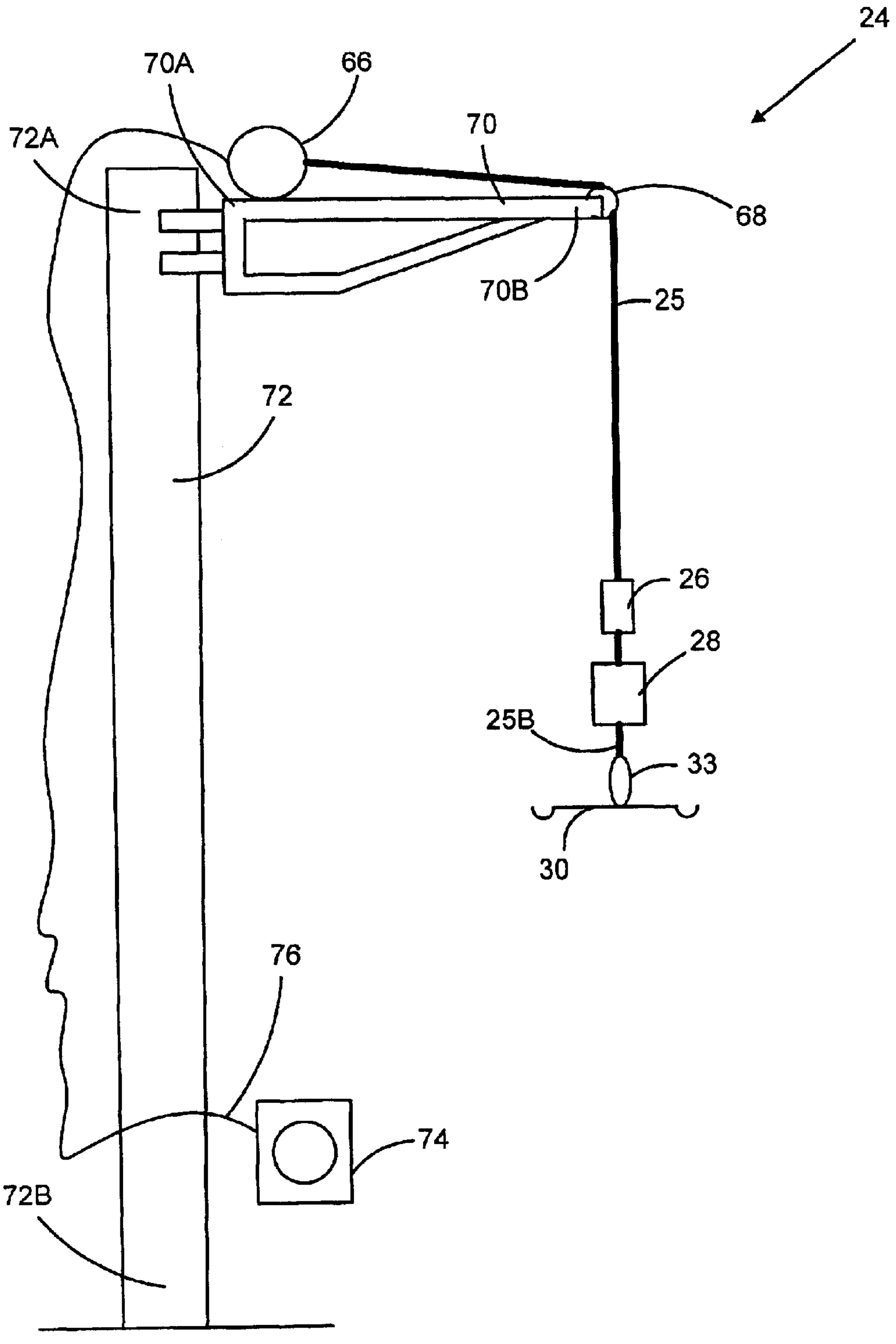
FIG. 3. is a side view of the traction member.

FIG. 3 shows one embodiment of the traction member (24). In this embodiment, an upright member (72) is attached at its first end (72A) to an arm member first end (70A). The upright member (72) is substantially vertical and the arm member (70) is substantially horizontal. A traction line (25) extends downwardly from the arm member second end (70B) to the tub (not shown). In this embodiment, the traction line (25) is extended and retracted by a winch (66). The traction line (25) extends from the winch (66) over a pulley (68) at the arm member second end (70B). A power source (74) connected to the winch (66) by a power cable (76) provides for operation of the winch (66).

The traction member (24) is positioned relative to the tub (12), however, the traction member (24) may be connected to the controlled therapeutic traction device (10) or it may be connected to another static point. In the embodiment illustrated in this figure, the upright member end (72B) could be attached to the controlled therapeutic traction device (10) or to a floor, wall, or other solid substrate (not shown). It is anticipated that a multitude of embodiments for the traction member (24) exist and many could be employed if they meet the operative requirement of the controlled therapeutic traction device (10).

The amount of traction applied to the patient (16) is controlled by the medical provider (not shown), however, a secondary traction control device (28) may be employed in operative engagement with the traction line (25). The secondary traction control device would operable by the medical provider (not shown), but also by the patient (16) who can reduce the amount of traction if it becomes unbearable or uncomfortable, or the patient (16) can increase the traction if it is comfortable and bearable. Because the amount of traction is a medical decision, a primary traction control device (26) is also provided for in operative engagement with the traction line (25). Like the secondary control device (28), the primary traction control device (26) controls the amount of tension applied by the traction line (25). However, the primary control device (26) is only useable or accessible to the medical provider (not shown) and not the patient (16). Further, the primary traction control device (26) can override the secondary traction control device (28) in regard to the amount of traction applied to the patient (16), or it could provide a preset range of tension within which the secondary traction control device (28) could operate. Thus, a medical provider (not shown) could set a specific amount of tension to be applied by the traction line (25) on the patient (16) or could set a range of tension in order that the patient (16) could employ the secondary traction control device (28) to modify the amount of tension within a medical provider's (not shown) preset range.

At the traction line second end (25B) is a harness connector (33). It allows for the connection of various types of harnesses (32) to the traction line (25). The various harnesses (32) are in turn attached to the patient (16) in order to apply tension to various parts of the patient's (16) body. Also shown, is a traction connector (30) as an option to further the type and position of the harness (32).

Figure 4:
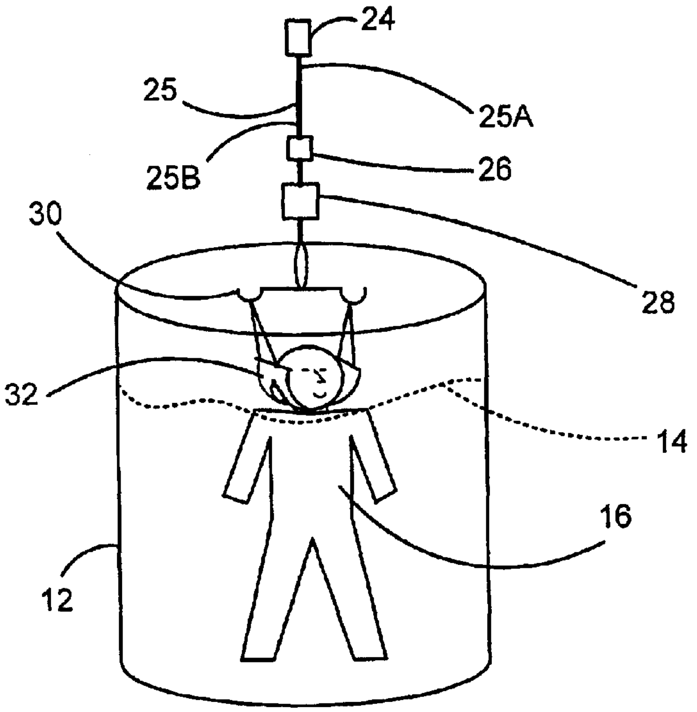
FIG. 4. is a side view of a patient suspended in the present invention.

FIG. 4. illustrates a patient (16) being held in traction by the controlled therapeutic traction device (10). In this embodiment, the traction connector (30) is used in conjunction with the harness (32) in order to provide tension to the cervical region of the patient (16). As illustrated in this figure, patient (16) is positioned inside the tub (12) with the fluid level (14) at the patient's (16) neck. The traction point (24) is positioned above the tub (12) and the traction line (25) is attached at its first end (25A) to the traction point (24) and by its second end (25B) to the patient (16). Also illustrated in this embodiment are the primary traction control device (26) and the secondary traction control device (28). Vertebral level specific traction harnesses (32) such as illustrated in this figure, allow traction to specific vertebral levels of the patient (16) while the patient (16) is suspended in the fluid (18). Such a harness (32) may also allow differential traction across vertebral disc spaces, and for specific angulated traction at that specific disc space.

Figure 5:
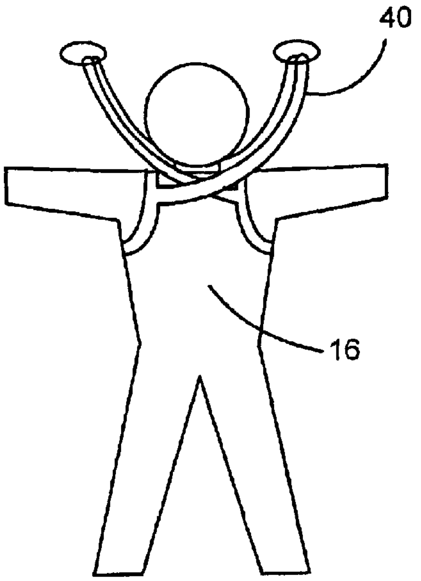
FIG. 5. is a side view of a harness for use with the present invention.

FIG. 5. illustrates an embodiment of the present invention that incorporates and upper thoracic traction harness (40) for application of tension to that region of the patient (16). As in FIG. 4., although not shown, the patient (16) is suspended in the tub (12) and the harness (40) is connected to the traction line (25).

Figure 6:
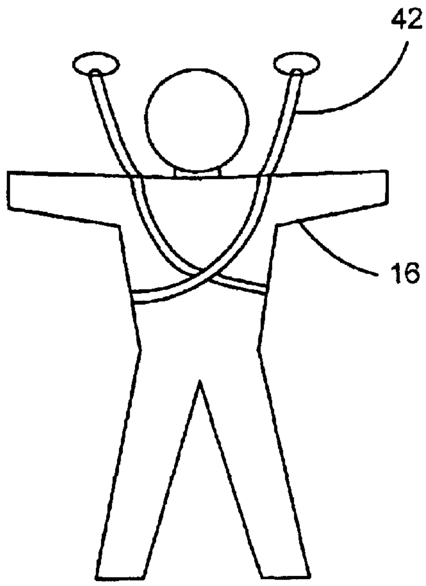
FIG. 6. is a side view of an alternate harness for use with the present invention.

FIG. 6. illustrates yet another embodiment of a harness (32). In this embodiment, a lower thoracic traction harness (42) is employed on the patient (16). Again, although not shown in this figure, the patient (16) is suspended in the fluid (18) within the tub (12) and the harness (42) is attached to the traction line (25). It is intended that the harnesses shown herein are for illustration purposes and it is anticipated that many other embodiments of harnesses could be employed with the present invention.

Figure 7:
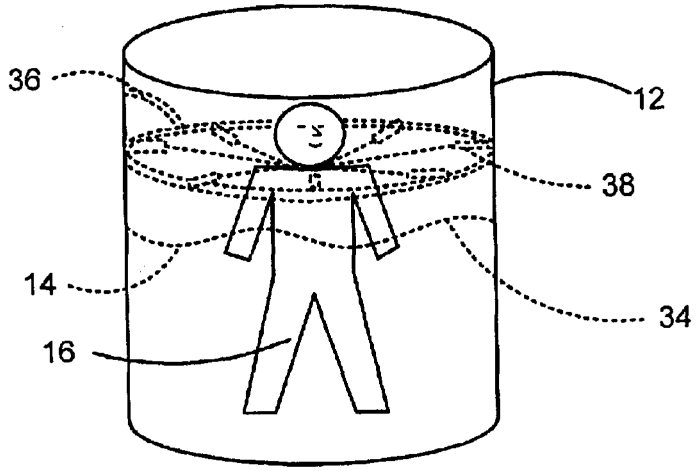
FIG. 7. is a perspective view of the present invention incorporating a neck irrigation ring.

FIG. 7. illustrates another option that can be employed in conjunction with the controlled therapeutic traction device (10). FIG. 7. illustrates a neck irrigation ring (34). The tubular neck irrigation ring (34) allows fluid (18) to be moved by a pump (not shown) through the neck irrigation ring (34). The fluid (18) is then expelled from the neck irrigation ring (34) through irrigation nozzles (38) at the patient (16). The neck irrigation ring (34) is intended for use in those instances in which it is desirable to keep those portions of the patient (16) that are above the fluid level (14) irrigated or moistened by the fluid (18). Thus, the neck irrigation ring (34) can apply a flow of fluid (18) to the patient (16) if the patient (16) is unable to immerse deeply enough in the tub (12) for cervical therapy.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A controlled therapeutic traction device for treating a patient by a caregiver comprising:

a tub having a vertical axis and capable of holding a fluid, said tub having an aperture through which said vertical axis extends;

said tub sized to allow said patient to fit within said tub;

said aperture sized to allow said patient entry and exit into said tub;

a traction member positioned substantially along said vertical axis adjacent to said aperture;

a traction line having a first end attached to said traction member, and a second end attached to a harness;

said harness removably attachable to said patient;

said traction line extending from said traction member through said aperture into said tub; and a traction applicator attachable to said patient at or below said patient's knee, and capable of applying a desired amount of downward force to said patient; and an amount of said fluid in said tub, wherein said fluid has a specific gravity sufficient to cause said patient, with said traction applicator attached to said patient, to float with said patient's head above said fluid.

2. The apparatus of claim 1, further comprising:

a secondary traction control device capable of controlling the amount of said downward force, said secondary traction control device operable by said patient.

3. A controlled therapeutic traction device for treating a patient by a caregiver comprising:

a tub having a vertical axis and capable of holding a fluid, said tub having an aperture through which said vertical axis extends;

said tub sized to allow said patient to fit within said tub;

said aperture sized to allow said patient entry and exit into said tub;

a traction member positioned substantially along said vertical axis adjacent to said aperture;

a traction line having a first end attached to said traction member, and a second end attached to a harness;

said harness removably attachable to said patient;

said traction line extending from said traction member through said aperture into said tub;

a traction applicator attachable to said patient and capable of applying a desired amount of downward force to said patient;

a secondary traction control device capable of controlling the amount of said downward force, said secondary traction control device operable by said patient; and a primary traction control device capable of controlling the amount of said downward force and overriding said secondary traction control device, said primary traction control device operable by said caregiver.

4. The apparatus of claim 1, wherein said fluid has a specific gravity of 1.2 or more.

5. The apparatus of claim 4, further comprising:

a pump in operative engagement with said tub.

6. The apparatus of claim 4 further comprising:

a heater in operative engagement with said tub.

7. The apparatus of claim 4, further comprising:

a sterilizer in operative engagement with said tub.

8. The apparatus of claim 4, further comprising:

a filter in operative engagement with said tub.

9. The apparatus of claim 4, further comprising:

a reservoir in operative engagement with said tub, said reservoir containing said fluid; and a reservoir pump in operative engagement with said reservoir and said tub, said reservoir pump capable of controlling the amount of said fluid in said tub.

10. The apparatus of claim 1, further comprising:

a pump in operative engagement with said tub.

11. The apparatus of claim 1, further comprising:

a heater in operative engagement with said tub.

12. The apparatus of claim 1, further comprising:

a sterilizer in operative engagement with said tub.

13. The apparatus of claim 1, further comprising:

a filter in operative engagement with said tub.

14. The apparatus of claim 1, further comprising:

a reservoir in operative engagement with said tub, said reservoir containing said fluid; and a reservoir pump in operative engagement with said reservoir and said tub, said reservoir pump capable of controlling the amount of said fluid in said tub.

15. A controlled therapeutic traction device for treating a patient by a caregiver comprising:

a tub having a vertical axis and capable of holding a fluid, said tub having an aperture through which said vertical axis extends;

said tub sized to allow said patient to fit within said tub;

said aperture sized to allow said patient entry and exit into said tub;

a traction member positioned substantially along said vertical axis adjacent to said aperture;

a traction line having a first end attached to said traction member, and a second end attached to a harness;

said harness removably attachable to said patient;

said traction line extending from said traction member through said aperture into said tub;

a traction applicator attachable to said patient and capable of applying a desired amount of downward force to said patient; and a charge generator in operative engagement with said tub capable of applying a charge to said fluid.

16. A controlled therapeutic traction device for treating a patient by a caregiver comprising:

a tub having a vertical axis and capable of holding a fluid, said tub having an aperture through which said vertical axis extends;

said tub sized to allow said patient to fit within said tub;

said aperture sized to allow said patient entry and exit into said tub;

a traction member positioned substantially along said vertical axis adjacent to said aperture;

a traction line having a first end attached to said traction member, and a second end attached to a harness;

said harness removably attachable to said patient;

said traction line extending from said traction member through said aperture into said tub;

a traction applicator attachable to said patient and capable of applying a desired amount of downward force to said patient; and a neck ring with an attached nozzle, said neck ring in operative engagement with said controlled therapeutic traction device such that said fluid can be transported though said neck ring and sprayed through said nozzle at said patient.

17. A controlled therapeutic traction device for treating a patient by a caregiver comprising:

a tub having a vertical axis and capable of holding a fluid, said tub having an aperture through which said vertical axis extends;

said tub sized to allow said patient to fit within said tub, wherein said patient is in a substantially upright position;

said aperture sized to allow said patient entry and exit into said tub;

said tub containing said fluid;

said fluid having a specific gravity of 1.2 or more;

a traction member positioned substantially along said vertical axis adjacent to said aperture;

a traction line having a first end attached to said traction member, and a second end attached to a harness;

said harness removably attachable to said patient;

said traction line extending from said traction member through said aperture into said tub;

a traction applicator attachable to said patient and capable of applying a desired amount of downward force to said patient;

a secondary traction control device capable of controlling the amount of said downward force, said secondary traction control device operable by said patient;

a primary traction control device capable of controlling the amount of said downward force and overriding said secondary traction control device, said primary traction control device operable by said caregiver;

a pump in operative engagement with said tub;

a heater in operative engagement with said tub;

a sterilizer in operative engagement with said tub;

a filter in operative engagement with said tub;

a reservoir in operative engagement with said tub, said reservoir containing said fluid;

a reservoir pump in operative engagement with said reservoir and said tub, said reservoir pump capable of controlling the amount of said fluid in said tub; and a charge generator in operative engagement with said tub cfapable of applying a charge to said fluid.

18. The apparatus of claim 17, further comprising:

a neck ring with an attached nozzle, said neck ring in operative engagement with said controlled therapeutic traction device such that said fluid can be transported though said neck ring and sprayed through said nozzle at said patient.

* * * * *